United States Patent
Heck et al.

(10) Patent No.: US 7,408,087 B2
(45) Date of Patent: Aug. 5, 2008

(54) PROCESS FOR MAKING UNSATURATED COCONUT AND/OR PALM NUT FATTY ALCOHOLS

(75) Inventors: Stephan Heck, Pulheim (DE); Norbert Klein, Mettmann (DE); Horst-Dieter Komp, Langenfeld (DE); Christiane Boehr, Leverkusen (DE); Norbert Huebner, Duesseldorf (DE); Alfred Westfechtel, Hilden (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 1197 days.

(21) Appl. No.: 09/874,899

(22) Filed: Jun. 5, 2001

(65) Prior Publication Data

US 2002/0035159 A1    Mar. 21, 2002

(51) Int. Cl.
*C07C 29/147* (2006.01)
*C07C 29/136* (2006.01)

(52) U.S. Cl. .................. 568/885; 568/876; 568/884

(58) Field of Classification Search .................. 568/885, 568/876, 884
See application file for complete search history.

(56) References Cited

U.S. PATENT DOCUMENTS 5,672,781 A * 9/1997 Koehler et al. .............. 568/885

FOREIGN PATENT DOCUMENTS

WO    WO 95/11210    * 4/1995

* cited by examiner

*Primary Examiner*—Elvis O Price
(74) *Attorney, Agent, or Firm*—John F. Daniels

(57) ABSTRACT

Unsaturated coconut and/or palm nut fatty alcohols having an iodine number in the range from 65 to 85, which essentially comprise unsaturated fatty alcohols and mixtures of saturated fatty alcohols of the formula (I):

$$R^1OH \qquad (I)$$

in which $R^1$ is a saturated or unsaturated, linear or branched alkyl radical having 12 to 20 carbon atoms, obtainable by fractionating coconut and/or palm nut fatty acid methyl esters to obtain a fraction containing predominantly $C_{16}$-$C_{18}$ portions, fractionating the $C_{16}$-$C_{18}$ fatty acid methyl ester fraction into a predominantly saturated distillate and a predominantly unsaturated bottom product, and hydrogenating the bottom product with retention of the double bonds to give the corresponding alcohols; are disclosed.

5 Claims, No Drawings

PROCESS FOR MAKING UNSATURATED COCONUT AND/OR PALM NUT FATTY ALCOHOLS

BACKGROUND OF THE INVENTION

1. Field of the Invention

The invention relates to unsaturated fatty alcohols which are obtained by subjecting coconut or palm nut fatty acid methyl esters to a two-fold fractionation and then hydrogenating, and to a process for the preparation of these fatty alcohols.

2. Statement of Related Art

Unsaturated fatty alcohols are important intermediates for a large number of products of the chemical industry, such as, for example, for the preparation of surfactants and skincare products. A review on this topic can be found, for example, by U. Ploog et al. in Seifen-Öle-Fette-Wachse [Soaps-Oils-Fats-Waxes] 109, 225 (1983). They are prepared from more or less unsaturated fatty acid methyl esters which can be hydrogenated, for example, in the presence of chromium- or zinc-containing mixed catalysts [Ullmann's Encyclopedia of Industrial Chemistry, Verlag Chemie, Weinheim, 4th Edition, Vol. 11, p. 436 ff]. The prior art is a large-scale process, as has hitherto also been carried out by the applicant, according to which animal fats and oils are used, and the unsaturated fatty alcohols produced after the hydrogenation are distilled at a still temperature of e.g. 220 to 250° C. and a reduced pressure of from 1 to 20 mbar—measured at the top of the column. Since the preparation of unsaturated fatty alcohols is associated with high costs, distillation has been carried out with as low a raw material loss as possible. In fact, in this way, it was possible to achieve a yield of about 90% of theory, and correspondingly a loss of 10%, although the products exhibited a marked intrinsic odor. A further disadvantage is that the fatty alcohols of the prior art have unsatisfactory storage and low-temperature behavior.

For application reasons, unsaturated fatty alcohols having iodine numbers of from 50 to 80 are particularly preferred since these have a solidification point which is favorable for use in cosmetic products. Unsaturated fatty alcohols having iodine numbers in the abovementioned range are currently largely based on animal raw materials. The desired iodine number range is set by blending different products having differing iodine number ranges. Adjustment of the iodine number range by distillative methods is not possible since the iodine number or iodine number range of animal-based fatty acids or fatty alcohols remains virtually constant during fractionation. However, animal fats have the disadvantage that they have a very heterogeneous structure. For example, animal fats contain nitrogen-containing compounds, such as amides or steroids, such as, for example, cholesterol, which are directly or indirectly responsible for the abovementioned unpleasant odor of the products. The nitrogen-containing compounds can become involved in secondary reactions, which impairs product stability, in particular oxidation stability, and leads to discolored products. In addition, because of the continuing BSE debate, products which are prepared using beef tallow are viewed extremely critically by the consumer. In the cosmetics market, there is therefore a continuous need for ever purer raw materials of ever higher quality, a demand which can usually only be met by ever more complex industrial processes and additional purification steps. In the case of unsaturated fatty alcohols, there is, in particular, the need for products having improved color and odor quality and a more advantageous low-temperature behavior. Added to this is the fact that in recent years consumer behavior has changed to the effect that consumers place very great value on purely vegetable products. The known vegetable fatty alcohols have iodine numbers in the range below 20 or very high iodine numbers above 100. Fatty alcohols having iodine numbers in the abovementioned range between 20 and 95, which is particularly preferred with regard to application technology, are not known. The blending of fatty alcohols having very different iodine numbers does not lead to satisfactory products. German Laid-open Specification DE-A1 4335781 (Henkel) discloses a process in which the triglycerides present in the vegetable fats or raw materials are firstly cleaved by pressurized cleavage into glycerol and fatty acids, and the latter are esterified with methanol, or the starting materials are directly transesterified to give the fatty acid methyl esters and then the esters are hydrogenated to give the alcohols, either the fatty acid methyl esters or the hydrogenation products being fractionated by removal of an amount of forerunnings such that the end product has an iodine number of from 20 to 110 and a conjuene content of less than 4.5% by weight. Whilst the process can be used for vegetable raw materials such as palm nut oil or coconut oil for the preparation of unsaturated fatty alcohols in the iodine number range 50 to 65 without problems, if said raw materials are used to produce unsaturated fatty alcohols in the iodine number range from 65 to 85, results are obtained which are surprisingly not entirely satisfactory.

The object of the present invention was consequently to provide unsaturated fatty alcohols based on coconut and/or palm nut oil which have iodine numbers in the range from 65 to 85 and, compared with animal-based unsaturated fatty alcohols, have greater oxidation stability and comparable or better low-temperature behavior. The aim was also to obtain extremely pure coupled products.

DESCRIPTION OF THE INVENTION

The invention provides unsaturated coconut and/or palm nut fatty alcohols having an iodine number in the range from 65 to 85, which essentially comprise unsaturated fatty alcohols and mixtures of saturated fatty alcohols of the formula (I)

$$R^1OH \qquad (I)$$

in which $R^1$ is a saturated or unsaturated, linear or branched alkyl radical having 12 to 20 carbon atoms, obtainable by (a) fractionating coconut and/or palm nut fatty acid methyl esters to obtain a fraction containing predominantly $C_{16}$-$C_{18}$ portions, (b) fractionating the $C_{16}$-$C_{18}$ fatty acid methyl ester fraction into a predominantly saturated distillate and a predominantly unsaturated bottom product, and (c) hydrogenating the bottom product with retention of the double bonds to give the corresponding alcohols.

Surprisingly, we have found that, by the process according to the invention, it is now possible for the first time to obtain unsaturated fatty alcohols, even those based on coconut and palm nut oil, in the iodine number range from 65 to 85 which have good color and oxidation stability and excellent low-temperature behavior; additionally, the products are virtually odorless. A further advantage is that a very pure palmitic acid methyl ester fraction is obtained as an intermediate, which can be further processed separately.

The invention further provides a process for the preparation of unsaturated coconut and palm nut fatty alcohols having an iodine number in the range from 65 to 85, which essentially comprise unsaturated fatty alcohols and mixtures of saturated fatty alcohols of the formula (I)

$$R^1OH \quad (I)$$

in which $R^1$ is a saturated or unsaturated, linear or branched alkyl radical having 14 to 20 carbon atoms, in which
   (a) coconut and/or palm nut fatty acid methyl esters are fractionated to obtain a fraction containing predominantly $C_{16}$-$C_{18}$ portions,
   (b) the $C_{16}$-$C_{18}$ fatty acid methyl ester fraction is fractionated into a predominantly saturated distillate and a predominantly unsaturated bottom product, and
   (c) the bottom product is hydrogenated with retention of the double bonds to give the corresponding alcohols.

1st fractionation

The fractionation of the coconut or palm nut fatty acid methyl esters can be carried out batchwise or continuously at reduced pressure. Heating can, for example, be by means of superheated steam, a still temperature of e.g. 220 to 250° C. normally prevailing. The actual fractionation takes place in a packed column containing low-pressure-loss internals. Suitable internals are, for example, arranged sheet-metal packings. Other examples can be found in RÖMPP Chemie Lexikon, Thieme Verlag, Stuttgart, 9th Edition, Vol. 3, p. 2305 (1990) under the heading "Kolonnen-Einbauten" [Column internals] and in the literature cited therein. The required fine vacuum of 1 to 20 mbar at the top of the column can be achieved, for example, using water-ring pumps and upstream steam jets. The pressure drop over the entire distillation unit should preferably be no more than 20 mbar. In this process, a fraction containing predominantly $C_8$-$C_{10}$ portions, a further fraction containing predominantly $C_{12}$-$C_{14}$ portions and finally a third fraction containing predominantly $C_{16}$-$C_{18}$ portions are obtained; the latter may be the bottom product. The weight ratio of distillate to bottom product is in the range from 30:70 to 35:65.

2nd fractionation

After a $C_{16}$-$C_{18}$ fatty acid ester fraction, which is also referred to as tailings, has been produced in the first fractionation, this fraction is separated in the second fractionation into a largely saturated distillate which comprises predominantly cetyl alcohol, and a largely unsaturated bottom product which consists predominantly of oleyl alcohol and has an iodine number in the range from 65 to 85, preferably 70 to 75. The second fractionation is carried out under comparable conditions to the first, although operating at about 220 to 250° C. and a reduced pressure of from 5 to 10 mbar. The weight ratio of distillate to bottom product is in the range from 10:90 to 15:85.

Hydrogenation

The final hydrogenation of the methyl ester fraction to obtain the double bonds can be carried out in a manner known per se, i.e. for example in the presence of commercially available zinc/chromium catalysts, at temperatures in the range from 250 to 350° C., and a hydrogen pressure of from 200 to 275 bar. The conjuene content of the products is in the range from 4 to 12% by weight, preferably 4.5 to 6% by weight, and the content of hydrocarbons is below 3% by weight, preferably below 1% by weight.

Industrial Applicability

The unsaturated coconut and/or palm nut fatty alcohols obtained by the process according to the invention are low in color and odor and have a particularly advantageous low-temperature behavior. They are therefore suitable as raw materials for the preparation of washing, rinsing and cleaning products, and also products for hair care and body care, in which they can be present in amounts of from 1 to 50% by weight, preferably 5 to 30% by weight, based on the compositions.

EXAMPLE

A $C_8$-$C_{18}$ coconut/palm nut fatty acid methyl ester was fractionated in a packed column containing low technical-grade pressure-loss internals at a still temperature of 200° C. and a head vacuum of 20 mbar. The two shorter-chain fractions containing the $C_8$-$C_{18}$ and $C_{12}$-$C_{14}$ portions were taken off and further processed separately. The $C_{16}$-$C_{18}$ fraction, which remained as the bottom product, was fractionated a second time in a second column at a still temperature of 250° C. and a head vacuum of 5 mbar, 15% by weight of palmitic acid methyl ester being produced as distillate, while in the still 85% by weight of a $C_{16}$-$C_{18}$ fatty acid methyl ester mixture remained, which had an iodine number of 72. The ester mixture was transferred to an autoclave and reduced therein in the presence of commercially available zinc/chromium catalysts at 300° C. and 250 bar with hydrogen to give the mixture of the corresponding fatty alcohols. The hydrogenation product freed from methanol had, according to gas-chromatographic and wet-chemical analysis, the characteristics as in Table 1:

TABLE 1

Characteristics for the hydrogenation product

| Composition | Portion [area %] | Characteristics | Value |
|---|---|---|---|
| Cetyl alcohol | 15.9 | Iodine number | 72 |
| Palmoleyl alcohol | 0.5 | Hydroxyl number | 211 |
| Margarinyl alcohol | 0.4 | Acid number | 0.02 |
| Stearyl alcohol | 10.7 | Saponification number | 0.3 |
| Oleyl alcohol | 62.3 | Hazen color number | 10 |
| Linolyl alcohol | 3.5 | Conjuene content | 4.6% by wt. |
| Linolenyl alcohol | 4.6 | Solidification point | 24° C. |
| Hydrocarbons | 2.1 | | |

What is claimed is:

1. A process for the preparation of a mixture of fatty alcohols having an iodine number in the range from 65 to 85 of the formula (I)

$$R^1OH \quad (I)$$

wherein $R^1$ is a saturated or unsaturated, linear or branched radical having from 14 to 20 carbon atoms, wherein the process comprises the steps of:
   (a) fractionating coconut and/or palm nut fatty acid methyl esters to produce a methyl ester fraction comprised substantially of $C_{18}$-$C_{18}$ portions,
   (b) fractionating the $C_{16}$-$C_{18}$ fatty acid methyl ester fraction of step (a) to produce a distillate comprised of predominantly saturated methyl esters and a bottom fraction comprised of substantially unsaturated methyl esters,
   (c) hydrogenating the bottom fraction to give the corresponding alcohols under conditions such that the carbon-carbon double bonds remain intact.

2. The process of claim 1 wherein the fractionating step of (a) is carried out batchwise or continuously.

3. The process of claim 1 wherein the fractionation step of (a) is carried out at a pressure of from 1 to 20 mbar.

4. The process of claim 1 wherein the fractionation step of (b) is carried out at a pressure of from 5 to 10 mbar.

5. The process of claim 1 wherein the distillate and the bottom fraction of step (b) are present in a weight ratio of from 10:90 to 5:85.

* * * * *